United States Patent [19]
Thayer

[11] 3,935,067

[45] Jan. 27, 1976

[54] INORGANIC SUPPORT FOR CULTURE MEDIA

[75] Inventor: Richard L. Thayer, Billings, Mont.

[73] Assignee: Wyo-Ben Products, Inc., Billings, Mont.

[22] Filed: Nov. 22, 1974

[21] Appl. No.: 526,376

[52] U.S. Cl. .............. 195/1.7; 195/100; 195/102; 195/116
[51] Int. Cl.² .... C12B 3/00; C12K 1/10; C12B 1/00
[58] Field of Search ............. 195/103.5 R, 100, 102, 195/103, 116, 1.7, 1.8

[56] References Cited
UNITED STATES PATENTS

| | | | |
|---|---|---|---|
| 1,832,593 | 11/1931 | Sziics | 195/102 |
| 2,476,785 | 7/1949 | Wallerstein | 195/116 |
| 2,769,750 | 11/1956 | Harris | 195/116 |
| 3,013,946 | 12/1961 | Lumb et al. | 195/116 |
| 3,224,946 | 12/1965 | Raymond | 195/116 |
| 3,580,811 | 5/1971 | Hidy | 195/100 |
| 3,887,430 | 6/1975 | Torney et al. | 195/1.7 |

OTHER PUBLICATIONS

Gieseking, J. E., "The Mechanism of Cation Exchange in the Mont–Morillonite–Beidellite–Nontronite Type of Clay Minerals" Soil Science, The Williams and Wilkins Co., 1939, p. 1.

Lyon, T. L., Buckman, H. O., and Brady, N.C., "The Nature and Properties of Soils," 5th Edition, Macmillan Co., 1952, pp. 86–88.

Grim, R. E., "Clay Minerology," 2nd edition, McGraw Hill, 1968 pp. 78–79 and pp. 251–253.

*Primary Examiner*—A. Louis Monacell
*Assistant Examiner*—C. A. Fan
*Attorney, Agent, or Firm*—Berman, Aisenberg & Platt

[57] ABSTRACT

Microorganisms and tissue cells are cultured in culture media which contain a growth support. Such support is often agar. All microorganisms and tissue cells which are grown and propagated on an agar support in a culture media are also grown and propagated under the same conditions on a solid or semi-solid support, consisting essentially of an inorganic water-swellable material and water, containing the same amounts of the same materials otherwise contained by the culture medium with the agar support.

22 Claims, No Drawings

INORGANIC SUPPORT FOR CULTURE MEDIA

BACKGROUND

The current technique for the propagation of microbial cultures includes admixing appropriate chemicals for a nutrient supply, water, and a support for the culture. Usually the support is the seaweed extract, agar. Agar is used primarily because it exhibits the desirable properties of:
1. water retention
2. a firm growing surface when cool
3. ease of handling when dissolved in boiling water
4. allowed mobility of the nutrient ions.

Agar also possesses undesirable properties. Agar is an organic compound, more specifically a polysaccharide; because of this it is susceptible to degradation and subsequent digestion by some types of microorganisms. Agar is also not tolerant to the entire range of pH that is sometimes employed in the culturing of microorganisms. Agar has water-retention properties that are of limited duration. In incubated petri dishes agar may dry out in a period of 1 to 2 weeks rendering the colony dormant or dead. In capped test tubes agar may last longer, but it still dries out in a period of several months. Besides the physical and chemical drawbacks associated with the use of agar as a microbial growth medium, there are also economic drawbacks. Agar has increased in price by a factor of 2 to 3 times over the past several years, and supplies seem to fluctuate depending on ocean currents and other harvesting conditions.

Due to the aforementioned drawbacks associated with the use of agar as a microbiological culture support medium, an alternative support medium that exhibits the desired agar characteristics and less of the undesired characteristics would be very valuable.

SUMMARY OF THE INVENTION

This invention relates to the use of inorganic waterswellable material, e.g. a naturally-occurring water-adsorbing clay mineral, as a support for growth and propagation of microbial and tissue-cell cultures in a culture medium. More particularly the invention relates to the use of, e.g., a water-adsorbing clay mineral as a substitute for agar as a growth support in culture media for all types of bacteria, tissue cultures (plant and animal), molds, yeasts, and other fungi. Culture conditions and culture media compositions are otherwise identical, i.e. except for the substitution of the agar support by that formed by the inorganic water-swellable material and water. The invention also includes culture media comprising either natural or artificial inorganic water-swellable support material and the preparation of such media.

All microorganisms and tissue cells which are grown and propagated on an agar or silica-gel support in an aqueous culture medium are also grown and propagated under the same conditions on a solid or semi-solid support (composed of an inorganic waterswellable material, such as a water-adsorbing clay mineral, and water) containing the same amounts of the same materials (e.g. minerals, sources of nitrogen, carbon, and energy, and sometimes vitamins or other growth factors) otherwise contained by the culture medium with the agar or silica-gel support. The media are sterilized, and inoculation with microorganisms or tissue cells is effected in accord with standard accepted procedures.

An ingredient furnishing energy is called the substrate. Substrates for culture media are generally, but not necessarily, organic. Four classes of inorganic compounds, e.g., serve as energy sources for chemolithotrophic bacteria. Cf. Stanier, Doudoroff and Adelberg, "The Microbial World", pages 416 to 419.

The invention has plural aspects:
a. aqueous microbial or tissue-cell culture media,
b. the use of an inorganic water-adsorptive mineral as a non-nutritive growth support in a culture medium,
c. the combination of a microorganism (fungus, mold, yeast or bacterium) with a culture medium having an inorganic growth support,
d. preparation of such culture media, and
e. using such culture media for growth and propagation of microorganisms or tissue cells.

The culture media are composed of nutrient matter (usually an organic substrate), inorganic non-nutritive water-adsorbing support material and water. A typical organic substrate is carbohydrate, such as sucrose and dextrose. Inorganic substrates include reduced nitrogen compounds, e.g. ammonia and nitrites; reduced sulfur compounds, e.g. $H_2S$, S and thiosulfates; hydrogen gas and ferrous iron.

When the inorganic support material is blended with the water, a thixotropic admixture is formed, and this admixture sets as a solid or semi-solid mass; it is used in this form, which is clearly non-particulate.

The natural or artificial inorganic support material is, e.g., a hydrated aluminum silicate, such as clay minerals, exemplified by montmorillonites and, more specifically, bentonite. It finds particularly advantageous use in static cultures.

DETAILS

Clay minerals in the montmorillonite category exhibit many of the characteristics that are desirable for a microbial or tissue-cell growth medium. Naturally-occurring swelling clays suitable as such growth supports include, e.g., bentonite, nontronite, beidellite, smectite, vermiculite, and swelling chlorite. These several clays vary considerably in water adsorptivity, the adsorbing capacity of vermiculite for water, e.g., is only about one third that of bentonite. The preferred clay mineral for this application is a high-swelling sodium-based bentonite that is composed primarily of montmorillonite.

Throughout the disclosure and claims "water-swellable" is applied only to material which swells at least 3-fold in contact with water. Preferred water-swellable inorganic supports swell at least 5-fold in contact with water. Still better water-swellable supports swell as much as 7- or 8-fold or even more in contact with water. High swelling sodium-based bentonite is reported to swell 10-fold in contact with water.

Major advantages for the use of a water-adsorbing clay mineral instead of agar as a culture support are:
1. Longer water retention — clay minerals, such as montmorillonite, have much better water-retention properties; in the range of 3 times or more than those of agar. The necessity of transferring stock cultures because of rapid dehydration is thus eliminated or substantially reduced, and incubation periods place less stress on the medium.

2. Cost — The cost of producing such clay minerals, e.g. montmorillonite, is much less than that for agar.

| Raw Bentonite | $12.00/ton |
| Refined Bentonite | $200.00/ton approx. |
| Agar - Retail | $44,800/ton |
| Agar - Wholesale | $16,000/ton |

3. Availability — The availability of montmorillonite is much greater than that of agar. Agar is a polysaccharide extract of a genus of seaweed (Gelidium) which grows in the Pacific Ocean, Indian Ocean and Japan Sea. Six hundred tons were imported into the United States in 1972 — there appears to be no surplus of agar and the price of agar has been rising. [The current consumption of agar in the United States of America amounts to several million pounds per year].

4. Inorganic versus Organic — Some organisms can utilize agar for nutrients; thus controlling the growth of such organisms is not possible on agar. Clay minerals do not have any usable organic material.

5. Field Preparation of Media — A dry clay mineral media base does not have to be heated to facilitate hydration; thus a sterile package of, e.g., bentonite media is readily added to distilled water in a "field" situation, and media are thus prepared without heat.

Raw unrefined clay minerals are useful as growth supports in culture media, but refining the clay minerals by passing a thin slurry thereof through a centrifuge yields a more desirable product. The increased desirability of the centrifuged product is demonstrated by the improved utility of growth media produced therewith. Grit and non-colloids are removed and a smoother more transparent product is obtained. The centrifuged product is superior because of (1) a higher percent water retention made possible by removal of extraneous material (i.e. grit and allophanes), (2) a more transparent and uniform color on which microbial growth is more readily observed, and (3) increased thixotropism, a property which provides for a "setting up" of the medium to yield a firm working surface for microbial growth. The addition of water and appropriate nutrient chemicals to purified clay mineral produces a growth medium of superior composition. The advantages of higher water retention and longer growth life are apparent. Other advantages not yet completely understood may account for the unique behavior of microbial colonies on the clay mineral growth medium.

The (w/v) relationship [corresponding to grams/cubic centimeter (g/cc)] between the inorganic support material and the water which swells it to a solid or semi-solid mass varies with the water adsorptivity and retentiveness of the inorganic material itself. For the purpose of the subject invention such relationship is ordinarily at least 3:100 for even the most water-adsorptive hydrated aluminum silicates, but generally at least 1:25, and preferably within the range of from 1:20 to 1:10 or possibly even 3:25 .

The water adsorptivity of the water-swellable hydrated aluminum silicate is a limiting factor on the ratio of support material to water in the formulation of any culture medium. The amount of hydrated aluminum silicate in any culture medium must be at least sufficient to adsorb all of the water used in that culture medium. Moreover, the amount of water in any culture medium cannot exceed that which, when blended with the hydrated aluminum silicate therein and nutrient materials, will permit the resulting blend to set into a solid or semi-solid mass. Hydrated aluminum silicate having the highest water adsorptivity and thus compatible with the lowest (w/v) relationship to yield a solid or semi-solid mass is preferred.

The hydrated aluminum silicate must thus likewise be one which, when mixed with water, forms a thixotropic mass that sets to a solid or semi-solid state. Thixotropism is an essential property of the aqueous mass produced with the hydrated aluminum silicate. Once the mass sets, it must be capable of retaining essentially all of its water, other than that lost by surface evaporation, for an extended period of time. Periods of water retention in excess of three, preferably in excess of 6, months or even longer are expected.

The solid or semi-solid support is pH stable over a large pH range. Such stability is reflected within the range of from pH 2 through pH 12.

Media according to this invention are useful for culturing diverse microorganisms and tissue cells. The microorganisms and tissue cells are prepared for culturing in accord with standard established procedures and are inoculated on such media in the generally-accepted and currently-employed manner. Illustrative of the microorganisms which are cultured on such media are fungi, such as Ascomycetes, e.g. *Penicillium notatum*, *Saccharomyces cerevisiae* and *Aspergillus fumigatus*; yeast-like fungi, e.g. *Candida albicans*; plant or animal parasites, such as *Phytophthora infestans* and Enterobacteriaceae, e.g. *Escherichia coli*, *Aerobacter aerogenes* and *Serratia marcescens*; Bacillacease, e.g. *Bacillus cereus*; bacteria, such as Micrococcaceae, e.g. *Sarcina lutea*; and Actinomycetaceae, e.g. *Actinomyces bovis*. Plant and animal tissue cells, such as cells of *Solanum tuberosum*, *Gallus Domesticus* embryonic fibroblasts and *Nicotinana glauca* are also cultured on media of this invention.

From the preceding discussion the artisan can make and use the subject invention throughout its various aspects. The following preferred specific embodiments are, therefore, merely illustrative and in no way limit either the scope of the remainder of the disclosure or of the claims appended hereto.

EXAMPLE 1

Blend 1000 milliliters (ml) of distilled water with 70 g of 200 mesh bentonite in a Waring Blender for 5 minutes to obtain a smooth thick slurry. Admix with the slurry the following dry nutrients:

| Sodium Nitrate | 2.0 grams |
| Potassium Chloride | 0.5 gram |
| Magnesium Glycerophosphate | 0.5 gram |
| Ferrous Sulfate Heptahydrate | 0.01 gram |
| Potassium Sulfate | 0.35 gram |
| Sucrose | 30.0 grams |

The pH of the resulting mixture is approximately 6.8. [Use lactic acid to adjust the pH to accommodate acidophilic organisms.] After thorough mixing, autoclave the resulting admixture (medium) to sterilize it. After autoclaving, pour the medium into petri plates or inject same into test tubes for subsequent inoculation.

Almost immediately the medium begins to exhibit thixotropic properties, which cause slight solidification.

Surface drying and the thixotropic effect eventually provide a semi-solid working surface for culturing microorganisms. The high waterretention properties of the bentonite yield a medium suitable for prolonged growth of inoculum.

Inoculate the medium on three petri plates with *Penicillium notatum*, *Aspergillus fumigatus* and *Candida albicans*, respectively, and culture the organisms under the same conditions otherwise employed for such culturing.

Replacing the 200-mesh bentonite with any other wateradsorbing hydrated aluminum silicate which swells at least 3-fold in contact with water, such as similarly finely-divided beidellite, nontronite or saponite, yields comparable results. Any of these minerals (in either refined or unrefined form) is substitutable for the bentonite in the following examples to obtain comparable results.

EXAMPLE 2

Repeat the medium preparation described in Example 1, replacing the dry nutrients called for therein by the following:

| | |
|---|---|
| Peptone (gelsate) | 10.0 grams |
| Lactose | 10.0 grams |
| Dipotassium Hydrogen Phosphate | 2.0 grams |
| Eosin Y | 0.4 gram |
| Methylene Blue | 0.065 gram |

Inoculate the resulting medium on separate petri plates with each of the bacteria, *Escherichia coli*, *Aerobacter Aerogenes* and *Serratia marcescens*, respectively, and culture the bacteria under conditions otherwise employed for such culturing. [Cf. "The Oxoid Manual", Third Edition, Oxoid Limited, Southward Bridge Road, London, England, 1971.]

EXAMPLE 3

Repeat the medium preparation described in Example 1, replacing the dry nutrients called for therein by the following:

| | |
|---|---|
| Beef Extract | 1.0 gram |
| Yeast Extract | 2.0 grams |
| Peptone (gelsate) | 5.0 grams |
| Sodium Chloride | 5.0 grams |

The pH of the resulting admixture is approximately 7.4. Inoculate the resulting medium on separate petri plates with each of the bacteria, *Escherichia coli*, *Bacillus cereus* and *Sarcina Lutea*, respectively, and culture the bacteria under conditions otherwise employed for such culturing.

EXAMPLE 4

Repeat the medium preparation described in Example 1, replacing the dry nutrients called for therein by the following:

| | |
|---|---|
| Peptone (gelsate) | 10.0 grams |
| Yeast Extract | 10.0 grams |
| Glucose | 10.0 grams |

The pH of the resulting admixture is approximately 7.0. The resulting medium is suitable for culturing yeasts and molds. Inoculate such medium on separate petri plates with *Penicillium notatum* and *Saccharomyces cerevisiae*, respectively, and culture these microorganisms under conditions otherwise employed for such culturing.

EXAMPLE 5

Repeat the medium preparation described in Example 1, replacing the dry nutrients called for therein by the following:

| | |
|---|---|
| Tryptone (casein) | 17.0 grams |
| Peptone (gelsate) | 3.0 grams |
| Dextrose | 2.5 grams |
| Sodium Chloride | 5.0 grams |
| Dibasic Potassium Phosphate | 2.5 grams |

The pH of the resulting admixture is approximately 7.3. The resulting medium is suitable for culturing bacteria and fungi. Inoculate such medium on separate petri plates with *Serratia marcescens*, *Bacillus cereus*, *Sarcina Lutea*, *Penicillium notatum*, *Actinomyces bovis* and *Phytophthora infestans*, respectively, and culture these microorganisms under conditions otherwise employed for such culturing.

EXAMPLE 6

Repeat the medium preparation described in Example 1, replacing the dry nutrients called for therein by the following:

| | | |
|---|---|---|
| Sucrose | 30.0 | grams |
| Glycine | 0.002 | gram |
| Indoleacetic Acid | 0.002 | gram |
| Kinetin | 0.0002 | gram |
| Myo-Inositol | 0.10 | gram |
| Nicotinic Acid | 0.0005 | gram |
| Pyridoxin Hydrochloride | 0.0005 | gram |
| Thiamin Hydrochloride | 0.0001 | gram |
| Ammonium Nitrate | 1.65 | grams |
| Potassium Nitrate | 1.90 | grams |
| Calcium Chloride | 0.44 | gram |
| Magnesium Sulfate Heptahydrate | 0.37 | gram |
| Monopotassium Phosphate | 0.17 | gram |
| Iron - EDTA | 0.0429 | gram |
| Boric Acid | 0.00625 | gram |
| Manganese Sulfate Monohydrate | 0.0223 | gram |
| Zinc Sulfate Heptahydrate | 0.0086 | gram |
| Potassium Iodide | 0.0008 | gram |
| Sodium Molybdate Dihydrate | 0.00025 | gram |
| Copper Sulfate Pentahydrate | 0.000025 | gram |
| Cobalt Chloride | 0.000025 | gram |

The resulting medium is suitable for culturing plant tissue cells. Inoculate such medium in separate test tubes with prepared tissue cells of *Solanum tuberosum* and *Nicotinana glauca*, respectively, and culture these tissue cells under conditions otherwise employed for such culturing. [Cf. Murashige, Toshio, and Skoog, Folks, "A Revised Medium for Rapid Growth and Bio Assays with Tobacco Tissue Cultures", *Physiologia Plantarum*, 15, 473, to 497, 1962. ]

EXAMPLE 7

Blend the following ingredients:

| | | |
|---|---|---|
| Sodium Nitrate | 0.50 | gram |
| Potassium Chloride | 0.125 | gram |
| Magnesium Sulfate Heptahydrate | 0.125 | gram |
| Ferrous Sulfate Heptahydrate | 0.0025 | gram |
| Potassium Sulfate | 0.0875 | gram |
| Sucrose | 7.50 | grams |
| Monosodium Phosphate | 0.125 | gram |
| Bentonite (200 mesh) | 15.0 | grams |
| Water (distilled) | 250 | milliliters | in a Waring Blender for 5 minutes. Autoclave the resulting blend at 15 pounds pressure for 20 minutes. Then pour petri plates. Inoculate the petri plates with *Penicillium notatum* and incubate for six days. The culture then covers 90 percent of the petri dishes. Many penicillin beads are present. No drying of the surface is observed.

EXAMPLE 8

Substitute the following ingredients for those specified in Example 7:

| | | |
|---|---|---|
| Nutrient Broth | 4.0 | grams |
| Bentonite (200 mesh) | 30 | grams |
| Water (distilled) | 500 | milliliters |

Inoculate the resulting poured petri plates with *Bacillus cereus*. The obtained growth is similar to that of the same organism on nutrient agar.

EXAMPLE 9

Substitute the following ingredients for those specified in Example 7:

| | | |
|---|---|---|
| Tryptone (casein) | 17.0 | grams |
| Peptone (gelsate) | 3.0 | grams |
| Sodium Chloride | 5.0 | grams |
| Dextrose | 2.5 | grams |
| Dibasic Potassium Phosphate | 2.5 | grams |
| Bentonite (200 mesh) | 60.0 | grams |
| Water (distilled) | 1.0 | liter |

Inoculate the individual resulting poured petri plates with *Aspergillus niger*, *Micrococcus flavus*, and *Saccharaomyces cerevisiae*, respectively. Good long-term growth was observed.

EXAMPLE 10

Substitute the following ingredients for those specified in Example 7:

| | | |
|---|---|---|
| Magnesium Sulfate Heptahydrate | 0.2 | gram |
| Dibasic Potassium Phosphate | 1.0 | grams |
| Ferrous Sulfate Heptahydrate | 0.05 | gram |
| Calcium Chloride | 0.02 | gram |
| Manganese Chloride | 0.002 | gram |
| Sodium Molybdate Dihydrate | 0.001 | gram |
| Ammonium Chloride | 1.0 | gram |
| Sodium Thiosulfate Heptahydrate | 7.0 | grams |
| Bentonite (200 mesh) | 60.0 | grams |
| Water (distilled) | 1.0 | liter |

Adjust the pH to neutral or slightly acid. This medium is suitable for culturing the obligate chemolithotrophic bacteria, *Thiobacillus thiooxidans*. The presence of any organic compound, including agar, in this medium would inhibit the growth of *Thiobacillus thiooxidans*.

EXAMPLE 11

Blend the following ingredients:

| | | |
|---|---|---|
| Lactalbumin Hydrolysate | 5.0 | grams |
| Sodium Chloride | 8.9 | grams |
| Potassium Chloride | 0.4 | gram |
| Calcium Chloride | 0.14 | gram |
| Magnesium Sulfate Heptahydrate | 0.1 | gram |
| Magnesium Chloride Hexahydrate | 0.1 | gram |
| Dibasic Sodium Phosphate | 0.06 | gram |
| Monobasic Potassium Phosphate | 0.06 | gram |
| Glucose | 4.0 | grams |
| Phenol Red (.5%) | 4.0 | grams |
| Sodium Bicarbonate | 0.35 | gram |
| Potassium Penicillin | 100,000 | I.U. |
| Streptomycin | 100,000 | I.U. |
| Bentonite (200 mesh) | 60.0 | grams |
| Water (distilled) | 1.0 | liter |

Autoclave the resulting medium at 15 pounds pressure for 20 minutes; then pour into clean, sterile tissue culture flasks. The resulting medium is suitable for culturing tissue cells of chick embryonic fibroblasts, *Gallus domesticus*. The bentonite used in this medium acts as a growth support base and/or an overlay after the fibroblast cells begin to grow.

EXAMPLE 12

The purification of sodium bentonite by centrifugation involves:

1. Making a slurry by blending 5% powdered bentonite and 95% distilled water. The blending does not have to be vigorous; any agitation will suffice, but the greater the agitation the faster the desired slurry will form. The resulting slurry has a typical viscosity of 90 cps, as measured by a Fann viscosity meter. The slurry contains the undesireable contaminants found in unpurified bentonite as mined (e.g. sand or $SiO_2$ and low colloidal clays, called allophanes). These contaminants are held in suspension in the slurry by the high colloidal material present.
2. The resulting slurry is introduced into a continuous flow Super-D-Canter centrifuge (model 3000; Sharples) with a G. force of 3180. Two fractions are collected:
   A. A thick solid mass of sand and low colloidal clay (approx. 2–3% by weight).
   B. A liquid slurry containing the high colloidal clay and water (approx. 97–98% by weight).

The viscosity of the high colloidal clay is now approximately 120 cps when measured on a Fann viscosity meter. This liquid slurry also has more pronounced thixotropic properties than the initial clay slurry.

3. The water is removed from the desired high colloidal clay material by any means that does not heat the clay to a temperature exceeding 250 degrees Fahrenheit. Above this temperature there is danger of destruction of some of the water-adsorbing properties of the clay.
4. The resulting dry clay product is ground to a 200 mesh particle size and used as a culture medium base.

Based on the preceding disclosure and specific examples the artisan will recognize that various changes and modifications of the invention can readily be made without departing from the spirit or scope thereof. The invention is not limited to the microorganisms or the tissue cells actually exemplified or disclosed; the culture media are of general application wherever a solid or semi-solid support mass is desired. The use of the subject inorganic support is independent of microorganisms being cultured and/or metabolic pathway.

What is claimed is:

1. In an aqueous microbial or tissue-cell culture medium which consists essentially of a support, nutrient matter and water, the improvement wherein the support is water-swellable to an extent of at least 3-fold in contact with sufficient water, and the support and water together constitute a solid or semi-solid non-particulate mass which is inorganic, is water-retentive, is thixotropic, and is a non-nutritive microbial or tissue-cell growth support.

2. Culture medium according to claim 1 wherein the support is a water-adsorbing clay which swells at least 5-fold in contact with water.

3. Culture medium according to claim 1 wherein the support is a hydrated aluminum silicate.

4. Culture medium according to claim 1 wherein the support is a montmorillonite.

5. Culture medium according to claim 1 wherein the support is bentonite.

6. Culture medium according to claim 1 wherein the support is refined clay.

7. Culture medium according to claim 1 wherein the nutrient matter comprises substrate which consists essentially of means for microbial or tissue-cell growth and propagation, and the support is stable over a pH range of from pH 2 through pH 12.

8. Culture medium means according to claim 7 for static microbial or tissue-cell growth and propagation.

9. Culture medium according to claim 7 wherein the substrate is organic substrate.

10. Culture medium according to claim 7 wherein the water-swellable support constitutes from 4 to 12 percent by weight, based on the weight of the water in the medium.

11. Culture medium according to claim 9 wherein the organic substrate is carbohydrate.

12. Culture medium according to claim 7 further comprising fungi.

13. Culture medium according to claim 7 further comprising mold.

14. Culture medium according to claim 7 further comprising yeast.

15. Culture medium according to claim 7 further comprising bacteria.

16. Culture medium according to claim 7 further comprising tissue cells.

17. A process for preparing culture medium according to claim 1 which comprises blending the water with sufficient wateradsorbing clay to obtain a smooth thick slurry, admixing the organic substrate and the other nutrient matter with the slurry, sterilizing the resulting admixture, and permitting the sterilized product to set to a solid or semi-solid mass.

18. A process which comprises inoculating culture medium according to claim 1 with a species of microorganism and culturing the species on the medium.

19. A process which comprises inoculating culture medium according to claim 1 with tissue cells and culturing the tissue cells on the medium.

20. In culturing microorganisms or tissue cells which may be grown and propagated on an agar or silica-gel support in an aqueous culture medium, the improvement wherein the agar or silica-gel support is replaced by a support which is water-swellable to an extent of at least 3-fold in contact with sufficient water, and the support and water together constitute a solid or semi-solid non-particulate mass which is inorganic, is water-retentive, is thixotropic, and is a non-nutritive microbial or tissue-cell growth support.

21. Culture medium according to claim 1 wherein the (w/v) relationship between the inorganic support and the water which swells it to a solid or semi-solid mass is within the range of from 3:100 to 3:25.

22. Culture medium according to claim 1 wherein the amount of water-swellable support is sufficient to adsorb all of the water, and the amount of water is sufficient, when blended with the nutrient matter and support, to permit the resulting blend to set into a solid or semi-solid mass.

* * * * *